(12) United States Patent
Xu et al.

(10) Patent No.: US 8,989,708 B2
(45) Date of Patent: Mar. 24, 2015

(54) NETWORK DEVICE ACCESS ID ASSIGNMENT AND MANAGEMENT

(71) Applicants: Verizon Patent and Licensing Inc., Basking Ridge, NJ (US); Cellco Partnership, Basking Ridge, NJ (US)

(72) Inventors: Ce Xu, San Ramon, CA (US); Mingxing S. Li, San Jose, CA (US); Xuming Chen, San Ramon, CA (US); Priscilla Lau, Fremont, CA (US); Peter Li, West Orange, NJ (US); Said Hanbaly, Annandale, NJ (US)

(73) Assignees: Verizon Patent and Licensing Inc., Basking Ridge, NJ (US); Cellco Partnership, Basking Ridge, NJ (US)

( * ) Notice: Subject to any disclaimer, the term of this patent is extended or adjusted under 35 U.S.C. 154(b) by 32 days.

(21) Appl. No.: 13/898,961

(22) Filed: May 21, 2013

(65) Prior Publication Data

US 2014/0349609 A1 Nov. 27, 2014

(51) Int. Cl.
*G06F 15/16* (2006.01)
*H04W 12/06* (2009.01)
*H04W 74/00* (2009.01)

(52) U.S. Cl.
CPC ............ *H04W 12/06* (2013.01); *H04W 74/002* (2013.01)
USPC ........................................... 455/411; 455/410

(58) Field of Classification Search
USPC ................... 455/410, 411, 422.1, 426.1, 450; 370/252, 329, 331, 338
See application file for complete search history.

(56) References Cited

U.S. PATENT DOCUMENTS

2011/0019638 A1* 1/2011 Hamel et al. ................... 370/331
2013/0250888 A1* 9/2013 Lu ................................. 370/329

* cited by examiner

*Primary Examiner* — Sam Bhattacharya (57) ABSTRACT

One or more devices may receive an instruction to generate an index for a customer associated with a base station and may generate the index based on receiving the instruction. The index may include one or more spaces to store a corresponding one or more access identifiers (IDs) used to allow a user device to connect to the base station. The one or more devices may receive an instruction to add an access ID to the index; generate the access ID based on a format of the access ID, a customer type, a customer ID, or a space ID; store the access ID in one of the one or more spaces of the index; and provide the access ID to the user device and the base station. The access ID may permit the user device to connect to the base station to access a network via the base station.

20 Claims, 9 Drawing Sheets

Access ID Index
430

Customer Name: Company ABC
Customer ID: 0000000000000001
Type: Class 1

| Space ID | Access ID |
|---|---|
| 1 | 00000000000000001, 00000001 |
| 2 | 00000000000000001, 00000002 |
| 3 | |
| ... | ... |
| Z | 00000000000000001, Y |

Base Station Management
440

| Base Station ID | Access ID |
|---|---|
| Base station ID 1 | ID-1, ID-2 |
| Base station ID 2 | ID-1, ID-3 |
| Base station ID 3 | ID-2, ID-4 |
| Base station ID 4 | ID-3, ID-4, ID-5 |
| ... | ... |
| Base station ID YY | |

User Device Management
450

| User Device ID | Access IDs |
|---|---|
| User Device ID 1 | ID-1, ID-2, ID-3 |
| User Device ID 2 | ID-1 |
| User Device ID 3 | ID-2 |
| User Device ID 4 | ID-3 |
| ... | ... |
| User Device ID ZZ | |

NETWORK DEVICE ACCESS ID ASSIGNMENT AND MANAGEMENT

BACKGROUND

A user device sometimes uses an access identifier to connect to a base station to access a network. Managing a large quantity of access identifiers (e.g., when the network includes a substantial quantity of base stations) may be cumbersome and may sometimes result in the exhaustion of access identifiers. Further, an access identifier may not identify a customer that is associated with the base station, thereby making the customer/access identifier relationship difficult to manage.

DETAILED DESCRIPTION OF THE PREFERRED EMBODIMENTS

The following detailed description refers to the accompanying drawings. The same reference numbers in different drawings may identify the same or similar elements.

Systems and/or methods, as described herein, may generate and manage access identifiers (IDs) used by user devices to connect to network devices (e.g., base stations, such as femto cell type base stations) to access a network. In some implementations, an access ID (e.g., a close subscriber group ID (CSG ID) and/or some other type of ID) may uniquely identify information regarding a customer that provides access to the base station, such as the type of customer (e.g., an individual user, a company, an organization, etc.), an identifier of the customer, a department or group identifier, and/or some other information regarding the customer. As a result, the access ID may link to an associated customer and provide access to the base station.

In some implementations, a user device may use the access ID to connect to a femto cell type base station to alleviate network load from another type of base station (e.g., a macro type base station). Additionally, the user device may connect to the femto cell type base station to receive additional network resources as a result of alleviating the network load. Additionally, or alternatively, a data flow sent/received by a particular base station may receive a particular policy treatment based on the type of customer associated with the particular base station. For example, a data flow received by a base station associated with a class 1 type customer may be prioritized over a data flow received by a base station associated with a class 2 type customer. In some implementations, the customer, associated with the particular base station, may provide the access ID to particular user devices to allow the particular user devices to connect to the particular base station.

Figure 1A:
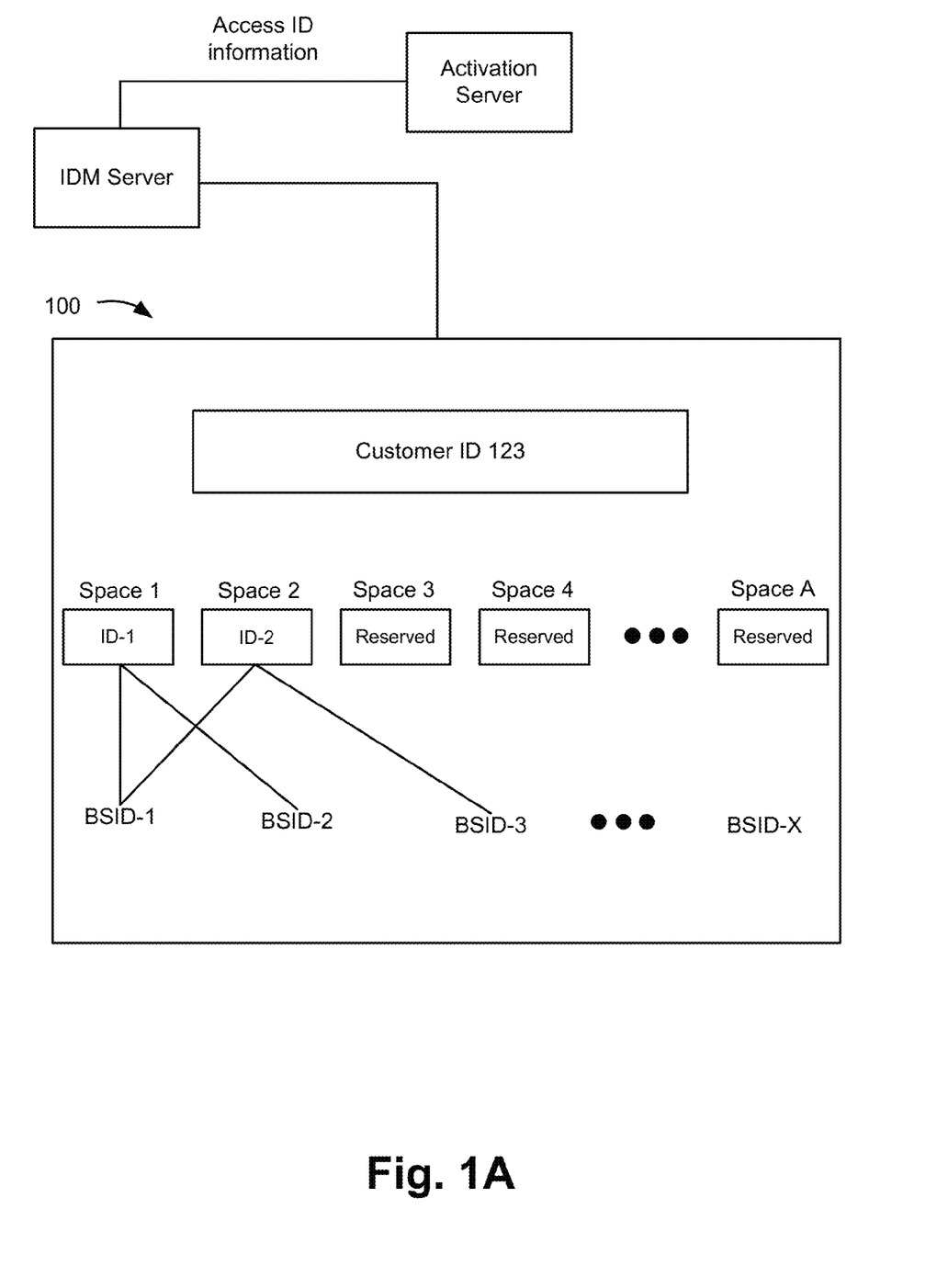
FIGS. 1A-1B illustrate an example overview of an implementation described herein.
Figure 1B:
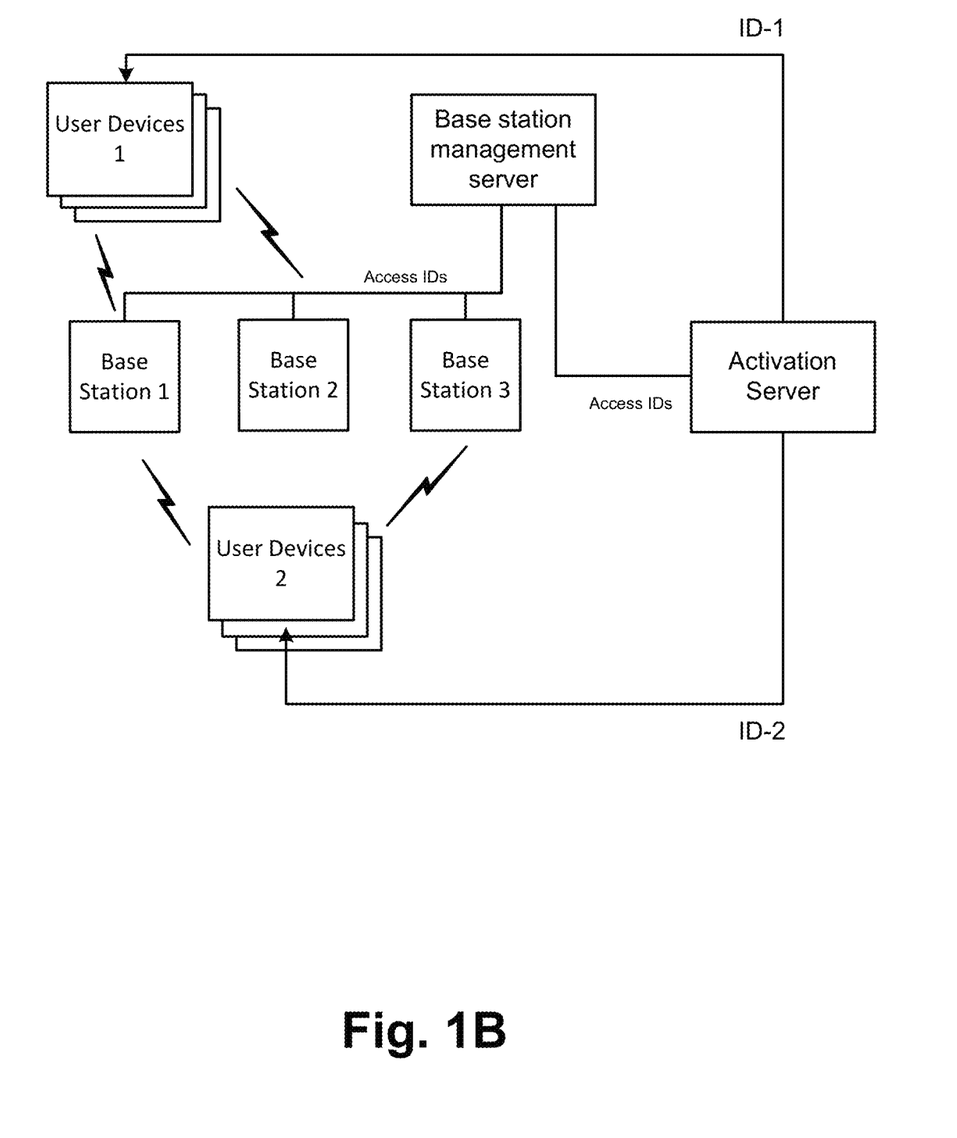

FIGS. 1A-1B illustrate an example overview of an implementation described herein. As shown in FIG. 1A, an ID management (IDM) server may receive information (e.g., from an activation server) that identifies access IDs associated with a customer (e.g., access IDs that the customer may use to connect to one or more base stations via a user device). In some implementations, the IDM server may store the access IDs in an access ID index (referred to as "index") 100 associated with the customer. As shown in FIG. 1A, index 100 may store information identifying one or more access IDs that the customer may use to connect to a base station via a user device. In some implementations, index 100 may include a particular quantity of fields (e.g., space 1 through space A, where A≥1) that store corresponding access IDs. As shown in FIG. 1A, some of the spaces may be reserved until an access ID is assigned to the space. For example, a customer may incur a charge (e.g., from a service provider that provides access to a network via a base station) based on a quantity of access IDs in use (e.g., access IDs stored by index 100).

As further shown in FIG. 1A, each access ID may be provided to one or more base stations (e.g., identified as base station ID (BSID)-1 through BSID-X, where X≥1). In some implementations, a user device may connect to a base station using an access ID provided to the base station. For example, an activation server may provide the user device with a list of one or more access IDs based on the base stations with which the user device is authorized to connect.

In an example shown in FIG. 1B, assume that each access ID corresponds to a particular group or department in an organization. For example, each access ID may include an identifier of the organization and an identifier of the group. Further, assume that each group is authorized to connect to a particular group of base stations (e.g., group 1 may connect to base stations 1 and 2, whereas group 2 may connect to base stations 1 and 3). That is, the access ID for group 1 (e.g. ID-1) may be provided to base stations 1 and 2 and the access ID for group 2 (e.g., ID-2) may be provided to base stations 1 and 3. Given these assumptions, user devices, associated with users of group 1 (e.g., user devices 1), may each receive ID-1 such that user devices 1 may connect to base stations 1 and 2 and may not connect to base station 3. Further, user devices, associated with users of group 2 (e.g., user devices 2), may each receive ID-2 such that user devices 2 may connect to base stations 1 and 3 and may not connect to base station 2. In some implementations, the activation server may communicate with a base station management server to provide activation IDs that may be used to connect to the base stations.

As described above, each access ID may uniquely identify information regarding the customer. As a result, access IDs, associated with a particular customer, may be provided to a particular base station, associated with the customer (e.g., a femto cell type base station), such that only user devices, authorized by the customer (e.g., user devices having an access ID for the particular base station), may connect to the particular base station. As described above, an index for a particular customer may include multiple fields to store multiple access IDs (e.g., one access ID per department). Additionally or alternatively, the index may include a single field to store a single access ID (e.g., for an individual user). Further, a particular access ID may be provided to one or more base stations associated with the customer. In some implementations, a data flow sent/received by a particular base station may receive a particular policy treatment based on the type of customer associated with the base station. For example, a data flow sent/received by a base station associated with a class 1 type customer may receive priority over a data flow sent/received by a base station associated with a class 2 type customer.

While the systems and/or methods are described in terms of managing access IDs used by user devices to connect to base stations, such as femto cell type base stations, in practice, the systems and/or methods are not so limited. For example, the systems and/or methods may be used to manage access IDs to allow user devices to connect to other types of network devices, such as routers, switches, gateways, or the like. Further, when describing implementations in terms of a "base station," the same implementation may also apply to another type of network device.

Figure 2:
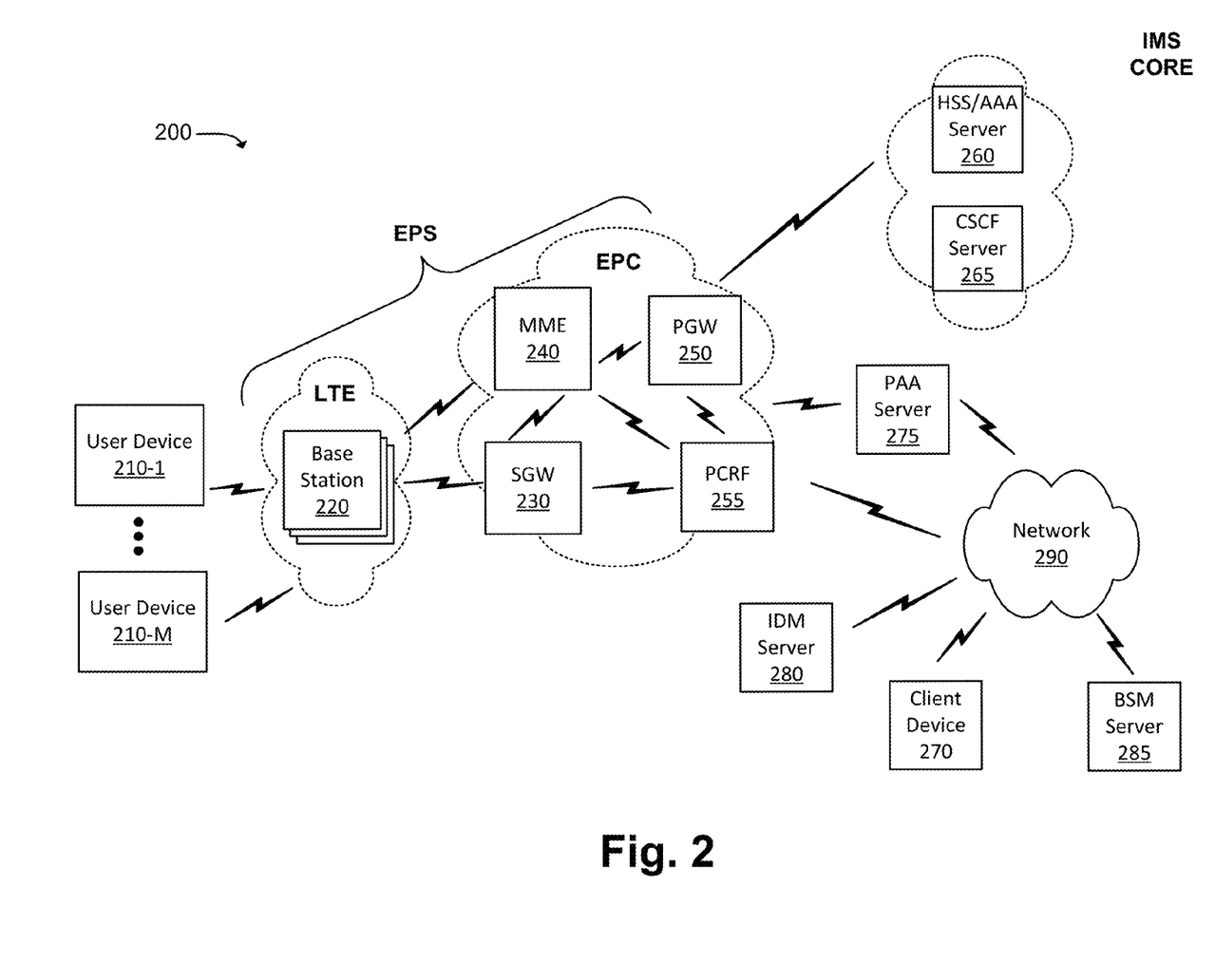
FIG. 2 illustrates an example environment in which systems and/or methods, described herein, may be implemented.

FIG. 2 is a diagram of an example environment 200 in which systems and/or methods described herein may be implemented. As shown in FIG. 2, environment 200 may include user devices 210, . . . , 210-M (where M≥1), a base station 220, a serving gateway 230 (referred to as "SGW 230"), a mobility management entity device 240 (referred to as "MME 240"), a packet data network (PDN) gateway (PGW) 250, a policy charging rules function (PCRF) 255, a home subscriber server (HSS)/authentication, authorization, accounting (AAA) server 260 (referred to as an "HSS/AAA server 260"), a call service control function (CSCF) server 265 (referred to as "CSCF server 265"), a client device 270, a provisioning and activation (PAA) server 275, an IDM server 280, a base station management (BSM) server 285, and a network 290.

In some implementations, one or more of the devices of environment 200 may perform one or more functions described as being performed by another one or more of the devices of environment 200. Devices of environment 200 may interconnect via wired connections, wireless connections, or a combination of wired and wireless connections.

Environment 200 may include an evolved packet system (EPS) that includes a long term evolution (LTE) network and/or an evolved packet core (EPC) that operate based on a third generation partnership project (3GPP) wireless communication standard. The LTE network may be a radio access network (RAN) that includes one or more base stations, such as eNodeBs (eNBs), via which user device 210 communicates with the EPC. The EPC may include SGW 230, MME 240, PGW 250, and/or PCRF 255 that enables user device 210 to communicate with network 290 and/or an Internet protocol (IP) multimedia subsystem (IMS) core. The IMS core may include HSS/AAA server 260 and/or CSCF server 265 and may manage authentication, connection initiation, account information, a user profile, etc. associated with user device 210. As shown in FIG. 2, the LTE network may include base station 220.

User device 210 may include a computation or communication device, such as a wireless mobile communication device that is capable of communicating with base station 220 and/or a network (e.g., network 290). For example, user device 210 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a smart phone, a laptop computer, a tablet computer, a camera, a personal gaming system, or another type of computation or communication device. User device 210 may send data to and/or receive data from network 290 via base station 220.

In some implementations, user device 210 may connect to a macro cell type base station 220 to send data to and/or receive data. In some implementations, user device 210 may connect to a femto cell type base station 220 to alleviate network load associated with the macro cell type base station 220 and/or to receive particular policy treatment. For example, user device 210 may receive an access ID (e.g., when connected to a macro cell type base station 220) to connect to a femto cell type base station 220.

Base station 220 may include one or more network devices that receive, process, and/or transmit traffic, such as audio, video, text, and/or other data, destined for and/or received from user device 210. In some implementations, base station 220 may be an eNB device and may be part of the LTE network. In some implementations, base station 220 may include a macro cell base station, a micro cell base station, a femto cell base station, and/or some other type of base station 220. Base station 220 may receive traffic from and/or send traffic to network 290 via SGW 230 and PGW 250. Base station 220 may send traffic to and/or receive traffic from user device 210 via an air interface. One or more of base stations 220 may be associated with a RAN, such as the LTE network. In some implementations, base station 220 may store information that identifies a policy that PCRF 255 may apply to a data flow received via base station 220. For example, base station 220 may mark the data flow to allow PCRF 255 to identify the policy to apply to the data flow. In some implementations, a particular base station 220 may be associated with a particular customer. Also, the particular base station 220 may store an access ID, associated with the particular customer, and may connect to user devices 210 that possess the access ID.

SGW 230 may include one or more network devices, such as a gateway, a router, a modem, a switch, a firewall, a network interface card (NIC), a hub, a bridge, a proxy server, an optical add-drop multiplexer (OADM), or some other type of device that processes and/or transfers traffic. SGW 230 may, for example, aggregate traffic received from one or more base stations 220 and may send the aggregated traffic to network 290 via PGW 250. In one example implementation, SGW 230 may route and forward user data packets, may act as a mobility anchor for a user plane during inter-eNB handovers, and may act as an anchor for mobility between LTE and other 3GPP technologies.

MME 240 may include one or more network devices that perform operations associated with a handoff to and/or from the EPS. MME 240 may perform operations to register user device 210 with the EPS, to handoff user device 210 from the EPS to another network, to handoff a user device 210 from the other network to the EPS, and/or to perform other operations. MME 240 may perform policing operations for traffic destined for and/or received from user device 210. MME 240 may authenticate user device 210 (e.g., via interaction with HSS/AAA server 260).

PGW 250 may include one or more network devices, such as a gateway, a router, a modem, a switch, a firewall, a NIC, a hub, a bridge, a proxy server, an OADM, or some other type of device that processes and/or transfers traffic. PGW 250 may, for example, provide connectivity of user device 210 to external packet data networks by being a traffic exit/entry point for user device 210. PGW 250 may perform policy enforcement, packet filtering, charging support, lawful intercept, and/or packet screening. PGW 250 may also act as an anchor for mobility between 3GPP and non-3GPP technologies.

PCRF 255 may include one or more network devices that store subscriber information, such as voice call and data rate plans or quotas for subscribers. PCRF 255 may provide network control regarding service data flow detection, gating, (Quality of Service) QoS, and/or flow based charging. Policies and rules regarding QoS may include policies and rules instructing user device 210 and/or network devices (e.g., base station 220, SGW 230, MME 240, PGW 250, etc.) to minimize packet loss, to implement a packet delay budget, to provide a guaranteed bit rate (GBR), to provide a particular latency, and/or to perform other activities associated with QoS. PCRF 255 may provide policies and rules to other network devices, such as HSS/AAAS server 260, and/or PGW 250, to implement network control. PCRF 255 may determine how a certain service data flow shall be treated, and may ensure that user plane traffic mapping and QoS is in accordance with a user's profile and/or network policies. In some implementations, PCRF 255 may apply a policy to a data flow received via a particular base station 220 (e.g., based on information stored by base station 220, based on a customer type associated with base station 220, and/or based on information received from PAA server 275 that identifies the policy for base station 220).

HSS/AAA server 260 may include one or more computing devices, such as a server device or a collection of server devices. In some implementations, HSS/AAA server 260 may manage, update, and/or store, in a memory associated with HSS/AAA server 260, profile information associated with user device 210 that identifies applications and/or services that are permitted for and/or accessible by user device 210, bandwidth or data rate thresholds associated with the applications or services, information associated with a user of user device 210 (e.g., a username, a password, a personal identification number (PIN), etc.), rate information, minutes allowed, and/or other information. Additionally, or alternatively, HSS/AAA server 260 may include a device that performs authentication, authorization, and/or accounting (AAA) operations associated with a communication connection with user device 210.

In some implementations, HSS/AAA server 260 may manage, update, and/or store profile information associated with a customer of base station 220 (e.g., a customer that owns, operates, and/or leases a femto cell type base station 220). For example, HSS/AAA server 260 may manage billing information that identifies a charge that may be based on a quantity of access IDs stored by an access ID index associated with the customer (e.g., access IDs that user devices 210 may use to connect to base station 220). Additionally or alternatively, the charge may be based on a customer type (e.g., a corporation, an individual, etc.) and/or some other factor. For example, the charge may be based on a policy that may be applied to a data flow received via base station 220 (e.g., higher charge amounts for higher GBR policies, lower latency policies, etc.). In some implementations, the charge may be debited from an account, associated with the customer, and credited to an account, associated with a service provider that provided access to network 290 via base station 220, the EPC, and/or the IMS core.

CSCF server 265 may include one or more computing devices, such as a server device or a collection of server devices. In some implementations, CSCF server 265 may process and/or route calls to and from user device 210 via the EPC. For example, CSCF server 265 may process calls, received from network 290, that are destined for user device 210. In another example, CSCF server 265 may process calls, received from user device 210, that are destined for network 290.

Client device 270 may include one or more computing devices, such as a desktop computing device, a portable computing device (e.g., a laptop, a tablet, a PDA, a mobile communication device, or the like), a server device, or some other type of computing device. In some implementations, client device 270 may receive (e.g., from a user of client device 270) an instruction to add an access ID to an index associated with a customer of base station 220 and/or to create an index for the customer (e.g., when an index does not exist). In some implementations, the instruction may identify a quantity of base stations 220 associated with the customer. Additionally or alternatively, the instruction may identify the type of customer, a policy to apply to data flows received via a particular base station 220 associated with the customer, and/or some other information. In some implementations, the instruction may be received via a point-of-sale transaction system, via a customer portal website, via an application, and/or via some other technique. In some implementations, the instruction may be provided to PAA server 275 to allow PAA server 275 to provision devices in environment 200 based on the instruction.

PAA server 275 may include one or more computing devices, such as a server device or a collection of server devices. For example, PAA server 275 may include an over-the-air (OTA) activation server, a mobile telephone activation server (MTAS), a provisioning system, and/or some other type of server or system. In some implementations, PAA server 275 may receive an instruction from client device 270 and may provision one or more devices in environment 200 based on the instruction. For example, PAA server 275 may direct PCRF 255 to apply a policy to data flows received via a particular base station 220 (e.g., when the instruction identifies the policy). Additionally or alternatively, PAA server 275 may provide information associated with the instruction to HSS/AAA server 260 (e.g., to allow HSS/AAA server 260 to apply charges to an account of the customer based on a quantity of access IDs stored by an index and/or to apply charges based on some other factor). In some implementations, PAA server 275 may direct IDM server 280 to create an index for a customer and/or to add an access ID to an existing index. Additionally or alternatively, PAA server 275 may direct BSM server 285 to add/remove an access ID to a particular base station 220.

IDM server 280 may include one or more computing devices, such as a server device or a collection of server devices. In some implementations, IDM server 280 may store an account index associated with a particular customer. As described above, IDM server 280 may receive an instruction to generate an account index and to add/remove access IDs to/from the account index.

BSM server 285 may include one or more computing devices, such as a server device or a collection of server devices. In some implementations, BSM server 285 may store information associated with base station 220. For example, BSM server 285 may store information that identifies a customer associated with base station 220 and a list of access IDs stored by base station 220 (e.g., access IDs that user device 210 may use to connect to base station 220). In some implementations, BSM server 285 may receive an instruction to add/remove an access ID to/from base station 220. In some implementations, BSM server 285 may communicate with base station 220 to provision base station 220 to add/remove the access ID to/from a storage associated with base station 220.

In some implementations, BSM server 285 may communicate with base station 220 to monitor the status of base station 220. For example, BSM server 285 may perform a ping test (or some other type of test) with base station 220 to determine whether base station 220 is operating within a predetermined performance parameter (e.g., a packet-loss percentage, a ping time, etc). In some implementations, BSM server 285 may detect an outage, associated with base station 220 (e.g., when base station 220 is underperforming with respect to the predetermined performance parameter), and may provide an alarm (e.g., an e-mail, a text message, a phone call, or the like) to a management party (e.g., maintenance personnel, account management personnel, etc.), associated with base station 220, when the outage is detected.

Network 290 may include one or more wired and/or wireless networks. For example, network 290 may include a cellular network, a public land mobile network (PLMN), a second generation (2G) network, a third generation (3G) network, a fourth generation (4G) network, a fifth generation (5G) network, and/or another network. Additionally, or alternatively, network 290 may include a wide area network (WAN), a metropolitan area network (MAN), a telephone network (e.g., the Public Switched Telephone Network (PSTN)), an ad hoc network, an intranet, the Internet, a fiber optic-based network, and/or a combination of these or other types of networks.

The quantity of devices and/or networks, illustrated in FIG. 2, is not limited to what is shown. In practice, there may be additional devices and/or networks; fewer devices and/or networks; different devices and/or networks; or differently arranged devices and/or networks than illustrated in FIG. 2. Also, in some implementations, one or more of the devices of environment 200 may perform one or more functions described as being performed by another one or more of the devices of environment 200. Devices of environment 200 may interconnect via wired connections, wireless connections, or a combination of wired and wireless connections.

Figure 3:
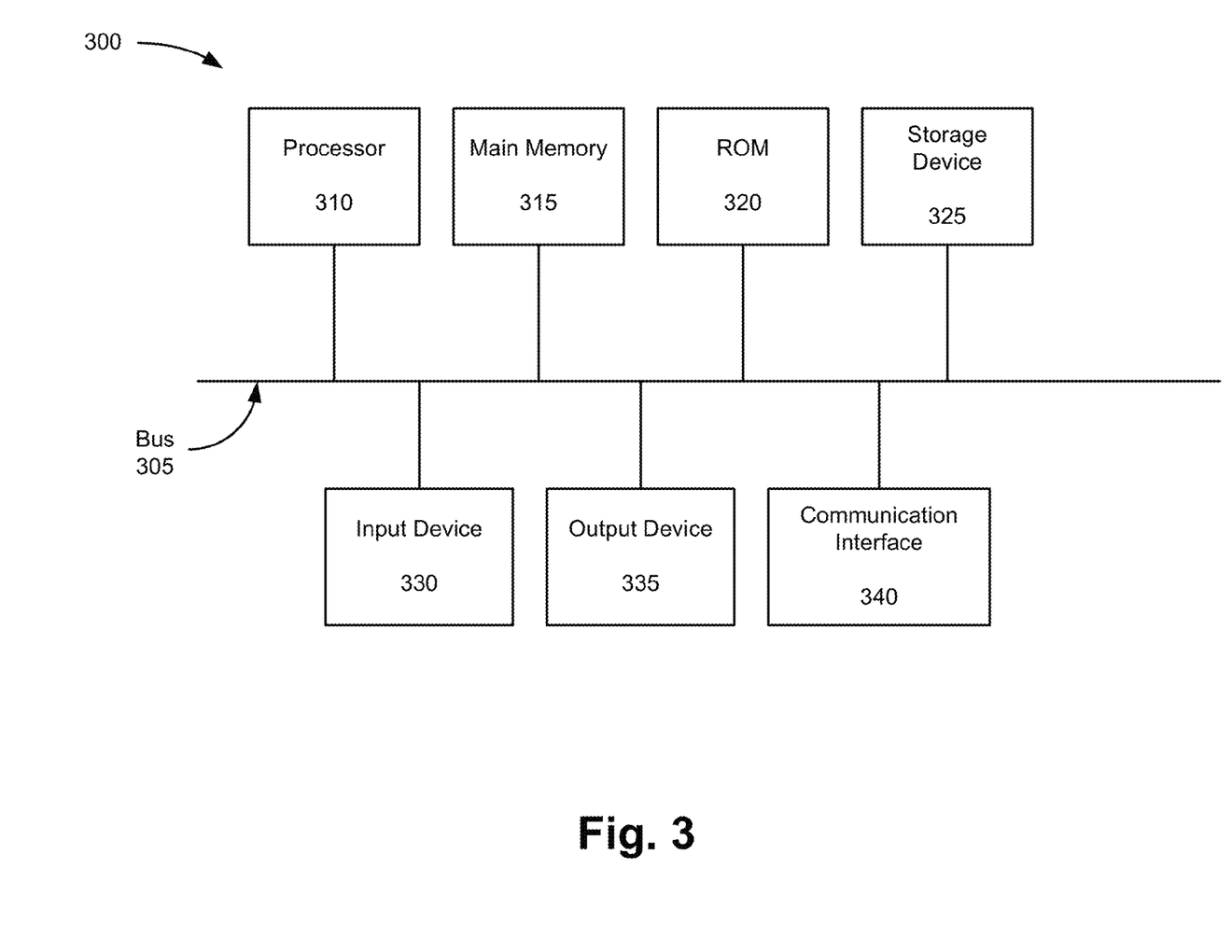
FIG. 3 illustrates example components of a device that may be used within the environment of FIG. 2.

FIG. 3 illustrates example components of a device 300 that may be used within environment 200 of FIG. 2. Device 300 may correspond to user device 210, base station 220, SGW 230, MME 240, PGW 250, PCRF 255, HSS/AAA server 260, CSCF server 265, client device 270, PAA server 275, IDM server 280, and/or BSM server 285. Each of user device 210, base station 220, SGW 230, MME 240, PGW 250, PCRF 255, HSS/AAA server 260, CSCF server 265, client device 270, PAA server 275, IDM server 280, and/or BSM server 285 may include one or more devices 300 and/or one or more components of device 300.

As shown in FIG. 3, device 300 may include a bus 305, a processor 310, a main memory 315, a read only memory (ROM) 320, a storage device 325, an input device 330, an output device 335, and a communication interface 340.

Bus 305 may include a path that permits communication among the components of device 300. Processor 310 may include a processor, a microprocessor, an application specific integrated circuit (ASIC), a field programmable gate array (FPGA), or another type of processor that interprets and executes instructions. Main memory 315 may include a random access memory (RAM) or another type of dynamic storage device that stores information or instructions for execution by processor 310. ROM 320 may include a ROM device or another type of static storage device that stores static information or instructions for use by processor 310. Storage device 325 may include a magnetic storage medium, such as a hard disk drive, or a removable memory, such as a flash memory.

Input device 330 may include a component that permits an operator to input information to device 300, such as a control button, a keyboard, a keypad, or another type of input device. Output device 335 may include a component that outputs information to the operator, such as a light emitting diode (LED), a display, or another type of output device. Communication interface 340 may include any transceiver-like component that enables device 300 to communicate with other devices or networks. In some implementations, communication interface 340 may include a wireless interface, a wired interface, or a combination of a wireless interface and a wired interface.

Device 300 may perform certain operations, as described in detail below. Device 300 may perform these operations in response to processor 310 executing software instructions contained in a computer-readable medium, such as main memory 315. A computer-readable medium may be defined as a non-transitory memory device. A memory device may include memory space within a single physical storage device or memory space spread across multiple physical storage devices.

The software instructions may be read into main memory 315 from another computer-readable medium, such as storage device 325, or from another device via communication interface 340. The software instructions contained in main memory 315 may direct processor 310 to perform processes that will be described later. Alternatively, hardwired circuitry may be used in place of or in combination with software instructions to implement processes described herein. Thus, implementations described herein are not limited to any specific combination of hardware circuitry and software.

In some implementations, device 300 may include additional components, fewer components, different components, or differently arranged components than are shown in FIG. 3.

FIGS. 4A-4E illustrate an example data structure 400 that may be stored by one or more devices in environment 200. In some implementations, a portion of data structure 400 may be stored in a memory of PAA server 275, IDM server 280, and/or BSM server 285. In some implementations, data structure 400 may be stored in a memory separate from, but accessible by, PAA server 275, IDM server 280, and/or BSM server 285. In some implementations, data structure 400 may be stored by some other device in environment 200, such as base station 220, PCRF 255, HSS/AAA server 260, and/or client device 270.

A particular instance of data structure 400 may contain different information and/or fields than another instance of data structure 400. In some implementations, data structure 400 may include example formats of an access ID, an example access ID index, an example list identifying access IDs stored by base stations 220, an example list identifying access IDs stored by user devices 210, an example list identifying alarm instructions, and an example list of data flow treatments to provide to data flows processed by base station 220.

As shown in FIGS. 4A-4E, data structure 400 may include bit frame field 410, bit value field 420, access ID index field 430, base station management field 440, user device management field 450, master index field 450, alarm management field 470, and/or data flow treatment field 480.

Figure 4A:
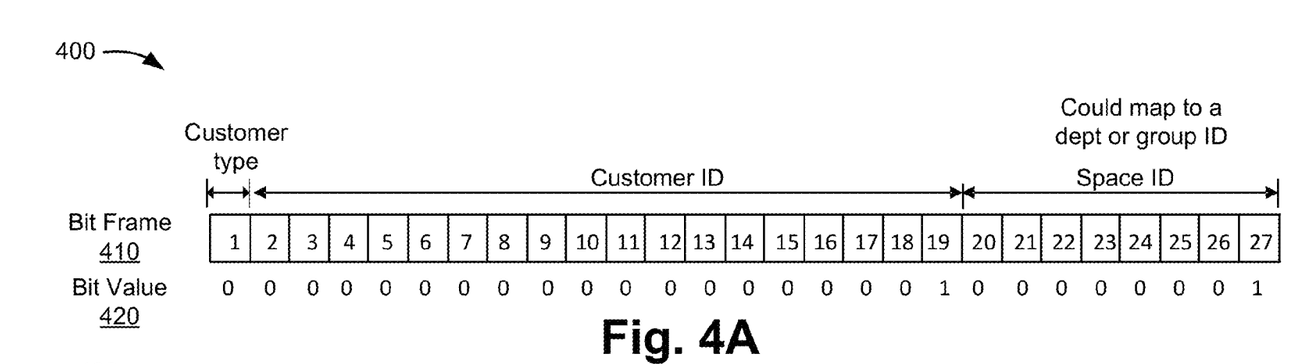
FIGS. 4A-4E illustrate an example data structure that may be stored by one or more devices in the environment of FIG. 2.

Bit frame field 410 may include information identifying a particular bit associated with an access ID. For example, as shown in FIG. 4A, the access ID may be 27 bits in length. In some implementations, the access ID may have some other length. As shown in FIG. 4A, each bit frame may include a particular bit value as shown in bit value field 420. In some implementations, particular bit frames may store bit values that identify a type of customer associated with the access ID. For example, the bit value stored by the first bit frame may indicate the type of customer (e.g., a large corporation type customer as indicated by the bit value "0"). In some implementations, the bit values stored by bit frames 2-19 may indicate a customer ID and the bit values for bit frames 20-27 may indicate a space ID associated with an index storing the access ID. In some implementations, the space ID may correspond to an organization ID, a group, ID, a department ID, or the like, associated with the customer. For example, a particular access ID may be provided to a particular base station 220 such that user devices 210, associated with a particular department in a corporation, may access the particular base station. In some implementations, the format of the access ID may vary from what is shown in FIG. 4A.

Figures 4B, 4C:
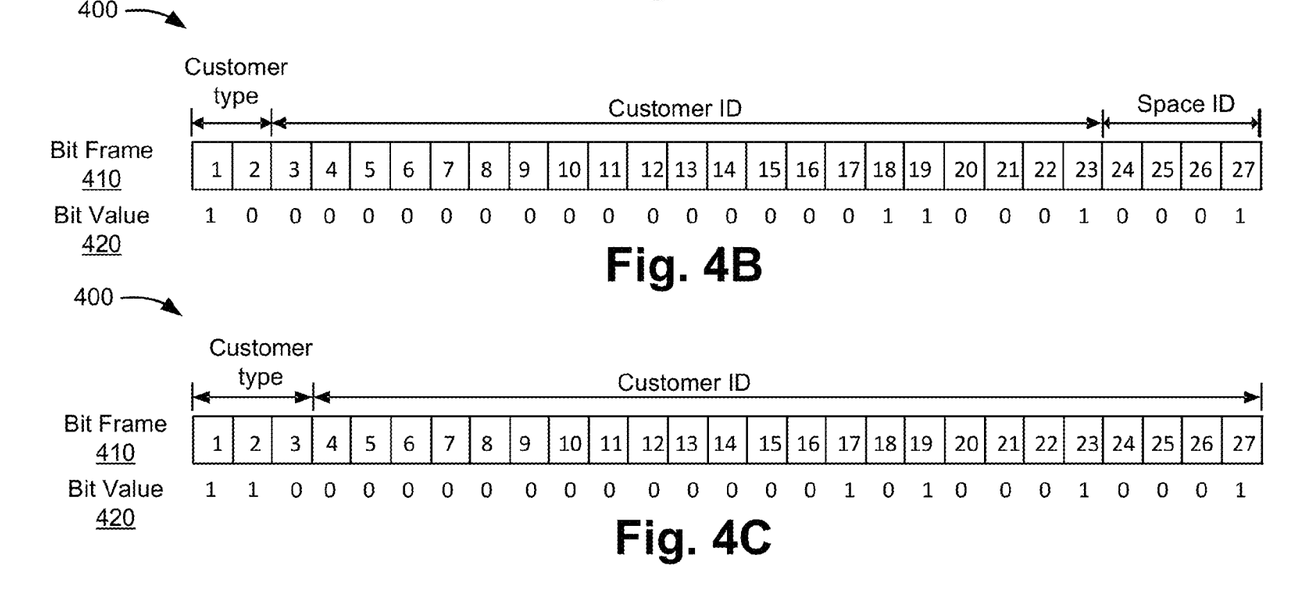

For example, referring to FIG. 4B, the bit values stored by the first two bit frames may indicate the type of customer (e.g., a medium-sized organization as indicated by the bit values "10"), whereas the bit values stored by bit frames 3-23 may indicate a customer ID, and the bit values stored by bit frames 24-27 may indicate a space ID. Another example of the format of the access ID is shown in FIG. 4C. As shown in FIG. 4C, the bit values stored by the first three bit frames may indicate the type of customer (e.g., an individual type customer as indicated by the bit values "110"), whereas the bit values stored by bit frames 4-27 may indicate a customer ID. As shown in FIG. 4C, the access ID may not include bit values that identify a space ID, for example, when the access ID is for an individual type customer (e.g., a customer that may only need one access ID in a corresponding index). In some implementations, the size of the index (e.g., the quantity of bit frames that store bit values that identify the space ID) may correspond to the type of customer. For example, an access ID for a large corporation type customer may have more bit frames to identify the space ID than an access ID for a medium-size organization (e.g., more space ID bit frames may correspond to more spaces in the index). In some implementations, the access ID may be in some other format not shown in FIG. 4A-4C. For example, bit frames that identify the customer type, customer ID, or space ID may be arranged differently than what is shown and may be arranged non-adjacent to each other.

Figure 4D:
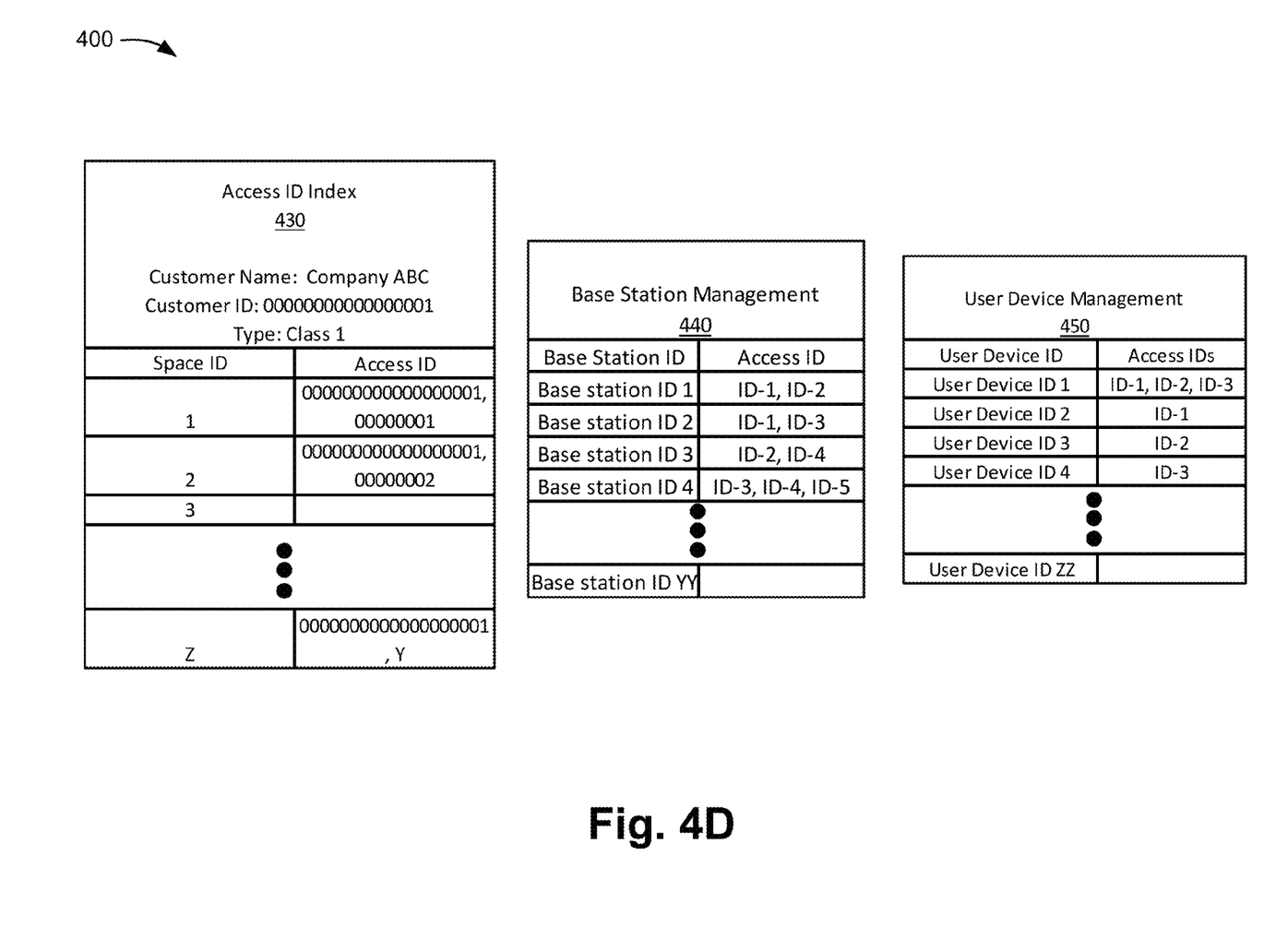

Referring to FIG. 4D, access ID index field 430 may illustrate an example index associated with a particular customer. As shown in FIG. 4D, access ID index field 430 may store information to identify a name of the customer, an ID of the customer, and a customer type (e.g., a class 1 type customer, a corporation type customer, etc.). In some implementations, a particular customer type may be associated with a particular billing rate charged by a service provider to access network 290 via base station 220. Additionally or alternatively, the particular customer type may be associated with a particular policy/QoS treatment. Additionally or alternatively, the particular customer type may be associated with a particular set of alarm instructions (as described in greater detail below).

As further shown in FIG. 4D, access ID index field 430 may store a space ID and a corresponding access ID. For example, IDM server 280 may receive an instruction to generate an index for a particular customer and to add/remove access IDs to/from the index. As described above, an index may include a quantity of spaces. In some implementations, one or more of the spaces may remain vacant until IDM server 280 stores an access ID in a particular space (e.g., based on receiving an instruction to add an access ID to the index and to store the access ID in an available space). In some implementations, the access ID may be a CSG ID or some other type of ID.

Base station management field 440 may store an identifier of base station 220 and a corresponding access ID stored by base station 220. In some implementations, BSM server 285 may store an access ID in base station management field 440 when receiving an instruction to associate the access ID with base station 220. In some implementations, BSM server 285 may provide the access ID to base station 220 when receiving the instruction to associated the access ID with base station 220. As described above, user device 210 may connect to base station 220 using the access ID. As a result, only user devices 210 storing the access ID may connect to base station 220. As shown in FIG. 4D, base station management field 440 may store a list of identifiers of respective base stations 220 and corresponding access IDs stored by the respective base stations 220. In some implementations, a particular base station 220 may store multiple access IDs. In some implementations, base station management field 440 may store information identifying a customer associated with base station 220.

User device management field 450 may store an identifier of user device 210 and a corresponding access ID stored by user device 210. In some implementations, PAA server 275 may store the access ID in user device management field 450 when receiving an instruction to associate an access ID with user device 210. In some implementations, PAA server 275 may provide the access ID to user device 210 when receiving the instruction to associate the access ID with user device 210 (e.g., using an over-the-air update process, a provider resource list (PRL) update process, and/or some other type of process to provide the access ID to user device 210). In some implementations, a particular user device 210 may store multiple access IDs.

Figure 4E:
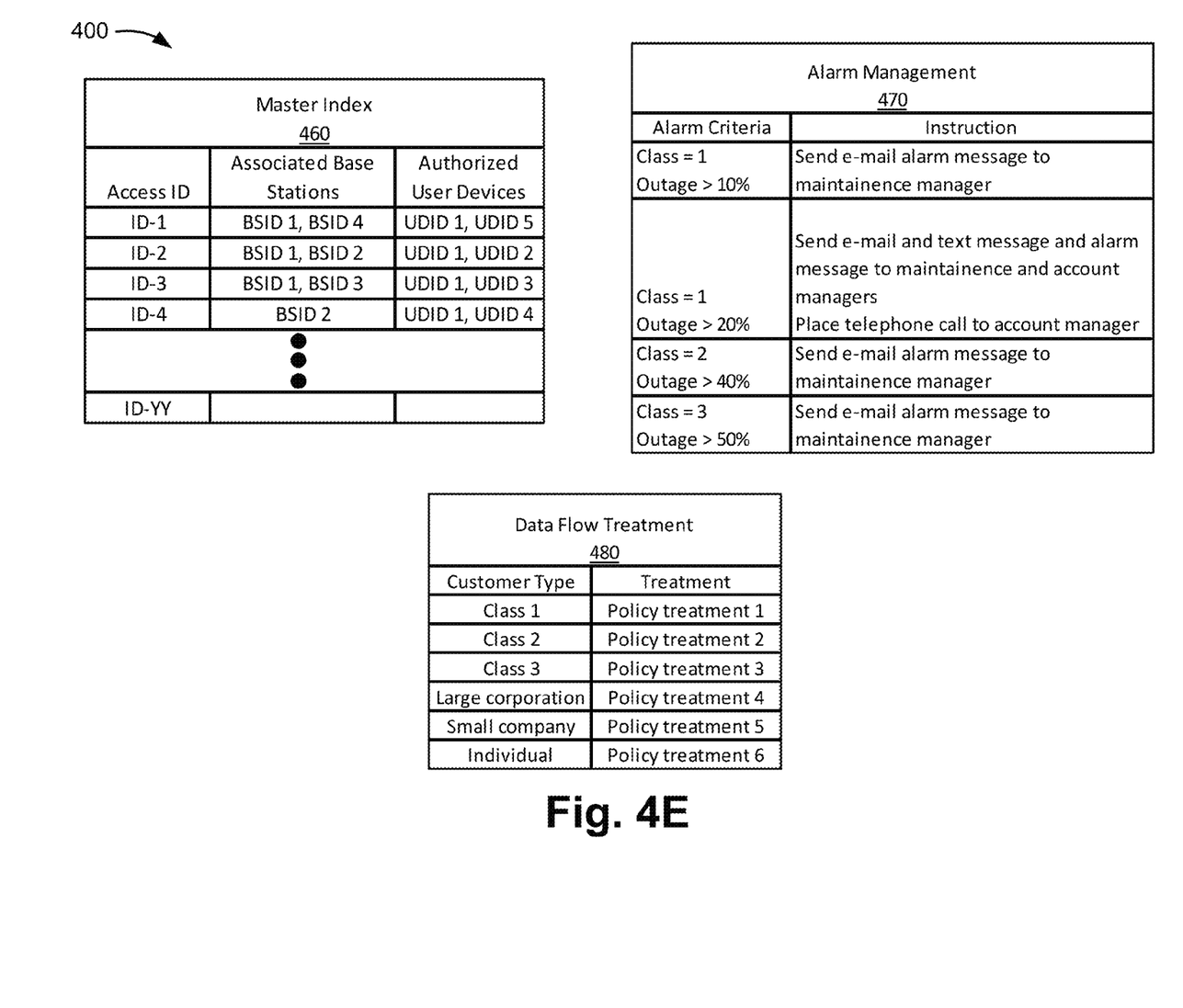

Referring to FIG. 4E, master index field 460 may store information that identifies an access ID, base stations 220 that correspond to the access ID, and user devices that correspond to the access ID. In some implementations, master index field 460 may be based on information stored by base station management field 440 and user device management field 450. As described above, an access ID may store information that identifies a customer type, a customer ID, and/or a space ID. Thus, information stored by base station management field 440, user device management field 450, and master index field 450 may be used to identify a quantity of access IDs, a quantity of base stations 220, and/or a quantity of user devices 210 associated with a particular customer and/or a particular group (e.g., space ID) associated with the particular customer. In some implementations, HSS/AAA server 260 may store billing information that identifies a charge based on the quantity of access IDs, base stations 220, and/or user device 210 associated with a customer.

Alarm management field 470 may store information that identifies alarm instructions that BSM server 285 may execute based on a set of criteria, such as a customer type and an outage percentage. For example, alarm management field 470 may store information to direct BSM server 285 to send an alarm when a particular quantity or percentage of base stations 220, associated with a particular customer, exceeds a particular threshold. In one example shown in FIG. 4E, alarm management field 470 may store a set of criteria, such as "class=1" and "outage>10%." As further shown in FIG. 4E, alarm management field 470 may store a corresponding instruction when the criteria are met. For example, alarm management field 470 may store an instruction to direct BSM server 285 to send an e-mail alarm message to a maintenance manager when an outage rate of base stations 220 exceeds 10% for a class 1 type customer or to send an e-mail, a text message, and a telephone call when the outage rate of base stations 220 exceeds 20% for a class 1 type customer. As further shown in FIG. 4E, alarm management field 470 may store an instruction to direct BSM server 285 to send an e-mail alarm message when an outage rate of base station 220 exceeds 40% for a class 2 type customer, or when an outage rate of base station 220 exceeds 50% for a class 3 type customer. That is, the alarm instruction may be based on the type of customer and/or the outage rate.

As described above, BSM server 285 may determine a status of base station 220 based on performing a performance test on base station 220 (e.g., to determine if the base station 220 is operating within a predetermined performance parameter, such as a ping time, a packet-loss rate, etc.). In some implementations, BSM server 285 may identify a base station outage rate for a particular customer based on a quantity of underperforming base stations 220 and a total quantity of base stations 220 associated with the particular customer (e.g., based on information stored by BSM server 285 that identifies base stations 220 associated with the particular customer).

In some implementations, alarm management field 470 may store other criteria than what is shown. For example, alarm management field 470 may store particular criteria for a particular customer or particular criteria for all customers of a particular type.

Data flow treatment field 480 may include information that identifies how a data flow, sent/received via a particular base station 220 associated with a particular customer type, may be treated. As described above, a particular base station 220 may be associated with a particular customer of a particular type. Based on the customer type, a policy treatment may be applied to data flows received via base station 220. For example, data flow treatment field 480 may store policy treatment information, such as rules, QoS treatments (e.g., GBR, maximum latency, maximum jitter, etc.), services, priority rules and/or other policy treatment information. In an example shown in data flow treatment field 480, data flows sent/received by base stations 220 associated with class 1 type customers may receive policy treatment 1 (e.g., a particular QoS treatment, a particular rule application, a particular network service, etc.). For example, base station 220 may store an access ID in a header of a packet in a data flow to allow SGW 230, MME 240, PGW 250, PCRF 255, CSCF server 265, and/or some other device to apply and/or enforce policy treatments for the data flow.

In some implementations, a call placed to a service provider (e.g., a provider that provides access to network 290 via base station 220) using a user device 210 connected to a base station 220 associated with a class 1 customer may be prioritized ahead of a call placed to the service provider using a user device 210 connected to base station 220 associated with a class 2 customer. For example, CSCF server 265 may receive an access ID from user device 210 when receiving a call instruction from user device 210. In some implementations, CSCF server 265 may prioritize the call instruction based on the customer type as indicated by the access ID (e.g., as described above with respect to FIGS. 4A-4C). As described above, PCRF 255 may communicate with SGW 230, MME 240, PGW 250, CSCF server 265, and/or some other device to apply and/or enforce policy treatments for data flows (e.g., based on information stored by data flow treatment field 480).

While particular fields are shown in a particular format in data structure 400, in practice, data structure 400 may include additional fields, fewer fields, different fields, or differently arranged fields than are shown in FIGS. 4A-4E. Also, the information stored by data structure 400 as described in FIGS. 4A-4E are described merely as examples. Other examples are possible and may differ from what was described with regard to FIGS. 4A-4E.

Figure 5:
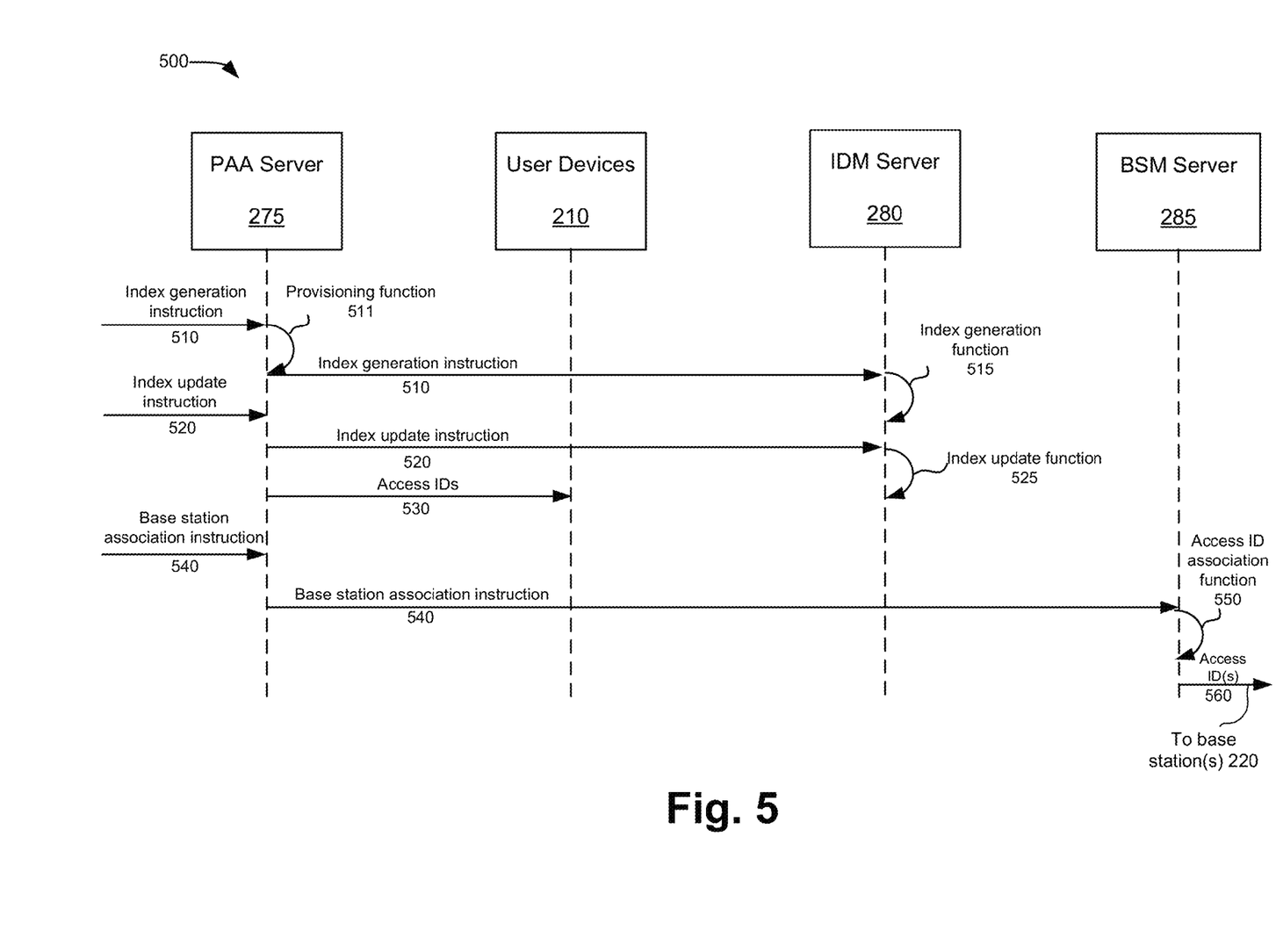
FIG. 5 illustrates a call flow diagram of example operations capable of being performed by an example portion of the environment of FIG. 2.

FIG. 5 illustrates a call flow diagram of example operations capable of being performed by an example portion 500 of environment 200. As shown in FIG. 5, portion 500 may include PAA server 275, user devices 210, IDM server 280, and BSM server 285. In some implementations, PAA server 275, user devices 210, IDM server 280, and BSM server 285 may include components and/or perform functions described above in connection with, for example, one or more of FIGS. 1-3. FIG. 5 may correspond to example operations to generate an index to store an access ID, update the index, and to associate an access ID with base station 220 and/or with user device 210.

In some implementations, PAA server 275 may receive index generation instruction 510 as part of a point-of-sale process, such as when a customer (or a managing party of the customer) provides an operator of PAA server 275 with a request to generate an index for the customer. For example, the request to generate the index for the customer may be based on a service-level agreement (SLA) between the customer and a service provider that provides access to network 290 via base station 220. As described above, the index may be used to store an access ID that may be provided to user device 210, and/or base station 220 to allow user device 210 to connect to base station 220. In some implementations, index generation instruction 510 may include information that identifies a quantity of base stations 220, associated with the customer, and/or a quantity of user devices 210 that may receive access IDs to access base stations 220. In some implementations, index generation instruction 510 may include information identifying policy treatments that a data flow, sent/received by a base station 220 associated with the customer, may receive. For example, PAA server 275 may determine a customer type and may identify policy treatments based on the customer type or based on the particular customer (e.g., as identified by a customer ID).

As shown in FIG. 5, PAA server 275 may perform provisioning function 511 based on receiving index update instruction 511. In some implementations, provisioning function 511 may direct PAA server 275 to provision devices in environment 200 in accordance with information associated with index generation instruction 510. For example, PAA server 275 may provide information to HSS/AAA server 260 that identifies billing charges that the customer may incur based on requesting an index, based on a customer type, and/or based on policy treatments. Additionally, or alternatively, PAA server 275 may provide policy treatment information to PCRF 255.

In some implementations, PAA server 275 may provide index generation instruction 510 to IDM server 280 (e.g., based on receiving index generation instruction 510). As shown in FIG. 5, IDM server 280 may perform index generation function 515 to generate and/or store an index based on receiving index generation instruction 510. For example, as part of index generation function 515, IDM server 280 may determine a customer type based on a quantity of base stations 220, associated with the customer, and/or a quantity of user devices 210 that may receive access IDs to access base stations 220 (e.g., as identified by index generation instruction 510). Additionally, or alternatively, IDM server 280 may determine a customer type based on information received from the customer (e.g., a request from the customer to be identified as a particular customer type). In some implementations, IDM server 280 may determine a customer type, such as a class 1 customer type, a class 2 customer type, a large corporation customer type, a small organization customer type, an individual user customer type, etc.

In some implementations, the customer type may be determined based on a threshold quantity of base stations 220, associated with the customer, and/or a threshold quantity of user devices 210 that may receive access IDs. As an example, a class 1 customer type may correspond to a customer whose quantity of base stations 220 exceeds 100 and whose quantity of user devices 210 exceeds 500. In some implementations, the thresholds, used to identify the customer types, may be based on a design decision such that particular customer types are associated with particular alarm instructions, particular billing rates, particular data flow policies/QoS treatments, etc.

In some implementations, IDM server 280 may generate the index based on determining the customer type. In some implementations, IDM server 280 may store the index in access ID index field 430 and may store a particular quantity of spaces based on the customer type. In some implementations, IDM server 280 may generate and store (e.g., in access ID index field 430) a customer ID having a particular value or length based on the customer type. For example, as described above with respect to FIGS. 4A-4C, a particular customer type may be associated with a customer ID of a particular value or length.

In some implementations, PAA server 275 may receive index update instruction 520 (e.g., via a web portal to provide index update instruction 520 to PAA server 275). For example, the customer may use login credentials to access the web portal (e.g., using client device 270) and to provide index update instruction 520 to PAA server 275. In some implementations, the web portal may be used to identify an access ID to add/remove to/from an index associated with the customer. For example, the web portal may present a list of available spaces in the index which may be used to store an access ID. Additionally or alternatively, the web portal may be used to identify an access ID to associate/remove with/from user device 210. For example, index update instruction 520 may identify user device 210 based on a user of user device 210, a telephone number of user device 210, or some other identifier associated with user device 210. In some implementations, index update instruction 520 may include an instruction to add/remove the access ID to/from the index and/or to associate/remove an access ID with/from user device 210 (e.g., based on input received by the web portal).

In some implementations, index update instruction 520 may include information that identifies the customer (e.g., based on login credentials used to access the web portal). For example, index update instruction 520 may include a customer ID that corresponds to the login credentials. In some implementations, PAA server 275 may encrypt index update instruction 520 to prevent unauthorized modification. In some implementations, PAA server 275 may provide, to HSS/AAA server 260, information regarding access IDs that are to be added/removed from the index and/or access IDs that are to be provided/removed from user device 210 such that HSS/AAA server 260 may update profile and/or billing information for the customer based on index update instruction 520.

As shown in FIG. 5, PAA server 275 may provide index update instruction 520 to IDM server 280 (e.g., based on receiving index update instruction 520). In some implementations, PAA server 275 may establish a secure channel with IDM server 280. In some implementations, IDM server 280 may receive index update instruction 520 via the secure channel (e.g., to prevent an unauthorized update of an index) and may perform index update function 525 based on receiving index update instruction 520. For example, IDM server 280 may decrypt index update instruction 520 (e.g., when index update instruction 520 is encrypted) and identify a particular index based on a customer ID included in index update instruction 520.

In some implementations (e.g., when index update instruction 520 includes an instruction add an access ID), IDM server 280 may generate the access ID in a manner that links the access ID with the customer. For example, IDM server 280 may generate the access ID based on a format of the access ID (e.g., based on information stored by bit frame field 410 and/or bit value field 420), the type of customer, the customer ID, and/or a space ID associated with the index. In some implementations, IDM server 280 may receive the format of the access ID from an operator of IDM server 280 (e.g., via a user interface of IDM server 280, via an application of client device 270, or via some other technique or source). In some implementations, the format of the access ID may be based on a design decision and may be based on the type of customer. That is, IDM server 280 may receive multiple access ID formats for multiple types of customers. Some examples of access ID formats are described above with respect to FIGS. 4A-4C.

In some implementations, IDM server 280 may store an access ID in an available space in the particular index, and/or remove an access ID from the particular index (e.g., when index update instruction 520 includes an instruction to remove an access ID from the index). For example, IDM server 280 may store the generated access ID in access ID index field 430 and/or remove an access ID from access ID index field 430.

As shown in FIG. 5, PAA server 275 may provide access IDs 530 to user devices 210 (e.g., based on receiving index update instruction 520). For example, PAA server 275 may provide access IDs 530 that are to be provided to particular user devices 210 based on index update instruction 520. In some implementations, PAA server 275 may provide access IDs 530 to user devices 210 using an OTA update process, a PRL update process, and/or some other type of update process. For example, PAA server 275 may provide access ID 530 to user device 210 when user device 210 connects to a base station 220 with which user device 210 is currently authorized to connect. In some implementations, user device 210 may store access ID 530 based on receiving access ID 530 such that user device 210 may connect to a base station 220 that corresponds to access ID 530. In some implementations, access ID 530 may include a CSG ID or some other type of ID.

As further shown in FIG. 5, PAA server 275 may receive base station association instruction 540 (e.g., via a web portal to provide base station association instruction 540 to PAA server 275). In some implementations, a customer may access the web portal using a set of login credentials and may use the web portal to identify an access ID to associate/remove with/from base station 220. For example, the web portal may present a list of base stations 220 associated with the customer (e.g., base stations 220 that the customer owns, leases, and/or has authorization to use). In some implementations, the list of base stations 220 may include a corresponding list of identifiers associated with base stations 220. Additionally, the web portal may present a list of access IDs that are available to the customer (e.g., access IDs that are stored by an index associated with the customer). In some implementations, the customer may generate base station association instruction 540 by using the web portal to associate an access ID with base station 220 (e.g., based on the list of access IDs and the list of base stations 220). That is, base station association instruction 540 may include information that identifies particular access IDs to associate with particular base stations 220 (e.g., based on the identifiers of the base stations 220).

In some implementations, PAA server 275 may provide base station association instruction 540 to BSM server 285 based on receiving base station association instruction 540. For example, PAA server 275 establish a secure channel with BSM server 285 and/or may encrypt base station association instruction 540 (e.g., to prevent unauthorized modification of base station association instruction 540). In some implementations, BSM server 285 may perform access ID association function 550 based on receiving base station association instruction 540. For example, BSM server 285 may decrypt base station association instruction 540 (e.g., when base station association instruction 540 is encrypted) and may identify access IDs to associate with a particular base station(s) 220 (e.g., based on the identifiers of the particular base station(s) 220). As shown in FIG. 5, BSM server 285 may provide access ID(s) 560 to the particular base station(s) 220. In some implementations, the particular base station(s) 220 may store access ID(s) 560 such that user devices 220 storing access ID(s) 560 may connect to the particular base station(s) 220.

While a particular series of operations and/or data flows have been described above with regards to FIG. 5, the order of the operations and/or data flows may be modified in other implementations. Further, non-dependent operations may be performed in parallel. For example, index update instruction 520 and base station association instruction 540 may be provided via the web portal using a single login session.

Figure 6:
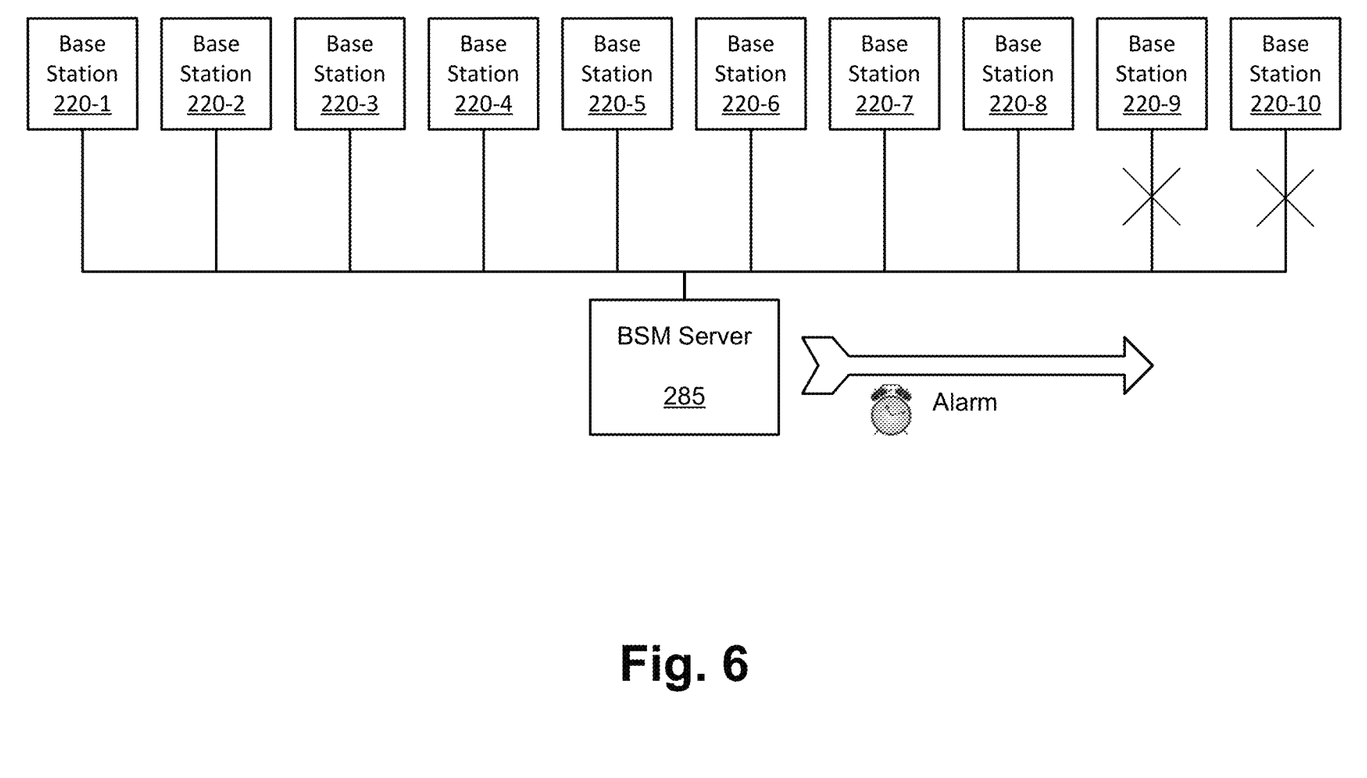
FIG. 6 illustrates an example implementation as described herein.

FIG. 6 illustrates an example implementation as described herein. As described above, BSM server 285 may connect with base stations 220 to monitor a status of base stations 220. For example, BSM server 285 may perform ping tests and/or some other type of status test to determine the status of base stations 220. In FIG. 6, assume that a particular customer is associated with base stations 220-1 through base stations 220-10. Further, assume that the particular customer is a class 1 type customer and that an alarm is to be provided when the outage rate of base stations 220 exceeds 10% (e.g., based on information stored by alarm management field 470). Further, assume that BSM server 285 determines that base stations 220-9 and 220-10 are experiencing an outage (e.g., when base stations 220-9 and 220-10 do not provide a response to a ping query provided by BSM server 285).

Given these assumptions, BSM server 285 may provide an alarm to a managing party associated with the particular customer in accordance with an alarm instruction stored by alarm management field 470. For example, BSM server 285 may provide an e-mail message to a particular e-mail address associated with a maintenance manager. Additionally or alternatively, BSM server 285 may provide a text message or a telephone call to the maintenance manager and/or some other party. In some implementations, the alert may cause a maintenance system to generate a trouble ticket such that the outage may be rectified.

As described above, outages for base stations 220, associated with a particular type of customer, may be identified and/or prioritized for repair ahead of outages for base stations 220 associated with another type of customer. For example, an alert for outages for base stations 220, associated with a class 1 type customer, may be provided when the outage rate exceeds 10%, whereas an alert for outages for base stations 220, associated with a class 2 type customer, may be provided when the outage rate exceeds 20%.

While a particular example is described with respect to FIG. 6, it will be apparent that the above description is merely an example implementation. Other examples are possible and may differ from what was described with regard to FIG. 6.

As described above, an access ID may uniquely identify information regarding a customer that owns, operates, leases, and/or has permission to access base station 220. As a result, access IDs, associated with a particular customer, may be provided to a particular base station 220, associated with the customer (e.g., a femto cell type base station 220), such that only user devices 210, authorized by the customer (e.g., user devices 210 having an access ID for the particular base station 220), may connect to the particular base station 220. As described above, an index for particular customer may include multiple fields to store multiple access IDs (e.g., one access ID per department). Additionally or alternatively, the index may include a single field to store a single access ID (e.g., for an individual user). Further, a particular access ID may be provided to one or more base stations associated with the customer. In some implementations, a data flow sent/received by a particular base station 220 may receive a particular policy treatment based on the type of customer associated with base station 220. For example, a data flow sent/received by a base station 220 associated with a class 1 type customer may receive priority over a data flow sent/received by a base station 220 associated with a class 2 type customer.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

No element, act, or instruction used in the present application should be construed as critical or essential unless explicitly described as such. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A method comprising:
   receiving, by one or more devices, an instruction to generate an index for a customer associated with a base station;
   generating, by the one or more devices, the index based on receiving the instruction to generate the index,
      the index including one or more spaces to store a corresponding one or more access identifiers (IDs) used to allow a user device to connect to the base station,
      the index identifying the customer or a customer type associated with the customer;
   receiving, by the one or more devices, an instruction to add an access ID to the index;
   generating, by the one or more devices, the access ID based on information that identifies a format of the access ID and one or more of the customer type, a customer ID associated with the customer, or a space ID associated with the index;
   storing, by the one or more devices, the access ID in one of the one or more spaces of the index, the access ID being associated with a base station ID that identifies the base station; and providing, by the one or more devices, the access ID to the user device and providing the access ID to the base station based on the base station ID,
the access ID permitting the user device to connect to the base station to access a network via the base station.

2. The method of claim 1, further comprising:
provisioning a network device to apply a particular policy to a data flow processed by the base station,
the particular policy being based on the customer type or the customer ID.

3. The method of claim 1, further comprising:
assessing a charge to an account of the customer based on a quantity of access IDs stored by the index and associated with the customer.

4. The method of claim 1, where the instruction to generate the index identifies a quantity of base stations associated with the customer or a quantity of user devices that are to receive access to the base station,
the method further comprising:
determining the customer type based on the quantity of base stations or the quantity of user devices,
where generating the index or generating the access ID is based on determining the customer type.

5. The method of claim 1, where the base station is one of one or more base stations,
the method further comprising:
monitoring a status of the one or more base stations to identify a particular base station, of the one or more base stations, that is underperforming with respect to a performance parameter; and
providing an alert when greater than a threshold quantity or a threshold percentage of the one or more base stations are underperforming,
the threshold quantity or the threshold percentage being based on the customer type or the customer ID.

6. The method of claim 1, where the format of the access ID includes a plurality of bits storing a corresponding plurality of bit values that identify the customer type, the customer ID, or the space ID.

7. The method of claim 1, where the base station is associated with a femto cell, a micro cell, or a macro cell.

8. The method of claim 1, where the access ID is a close subscriber group ID (CSG ID).

9. A system comprising:
one or more devices to:
receive an instruction to generate an index for a customer associated with a base station;
generate the index based on receiving the instruction to generate the index,
the index including one or more spaces to store a corresponding one or more access identifiers (IDs) used to allow a user device to connect to the base station,
the index identifying the customer or a customer type associated with the customer;
receive an instruction to add an access ID to the index;
generate the access ID based on information that identifies a format of the access ID and at least one of the customer type, a customer ID associated with the customer, or a space ID associated with the index,
the format of the access ID including a plurality of bits that store a corresponding plurality of bit values that identify the customer type, the customer ID, or the space ID;
store the access ID in one of the one or more spaces of the index,
the access ID being associated with a base station ID that identifies the base station; and
provide the access ID to the user device and provide the access ID to the base station based on the base station ID,
the access ID permitting the user device to connect to the base station to access a network via the base station.

10. The system of claim 9, where the one or more devices are further to:
provision a network device to apply a particular policy to a data flow processed by the base station,
the particular policy being based on the customer type or the customer ID.

11. The system of claim 9, where the one or more devices are further to:
assess a charge to an account of the customer based on a quantity of access IDs stored by the index and associated with the customer.

12. The system of claim 9, where the instruction to generate the index identifies a quantity of base stations associated with the customer or a quantity of user devices that are to receive access to the base station,
the one or more devices are further to:
determine the customer type based on the quantity of base stations or the quantity of user devices,
where when generating the index or when generating the access ID, the one or more devices are to generate the index or generate the access ID based on determining the customer type.

13. The system of claim 9, where the base station is one of a plurality of base stations,
the one or more devices are further to:
monitor a status of the plurality of base stations to identify a particular base station, of the plurality of base stations, that is underperforming with respect to a performance parameter; and
provide an alert when greater than a threshold quantity or a threshold percentage of the plurality of base stations are underperforming,
the threshold quantity or the threshold percentage being based on the customer type or the customer ID.

14. The system of claim 9, where the base station is associated with a femto cell, a micro cell, or a macro cell.

15. The system of claim 9, where the access ID is a close subscriber group ID (CSG ID).

16. A non-transitory computer-readable medium for storing instructions, the instructions comprising:
a plurality of instructions which, when executed by one or more processors, cause the one or more processors to:
receive an instruction to generate an index for a customer associated with a base station;
generate the index based on receiving the instruction to generate the index,
the index including one or more spaces to store a corresponding one or more access identifiers (IDs) used to allow a user device to connect to the base station,
the index identifying the customer or a customer type associated with the customer;
receive an instruction to add an access ID to the index;
receive information that identifies a format of the access ID, the format of the access ID including a plurality of bits that store a corresponding plurality of bit values that identify the customer type, a customer ID associated with the customer, or a space ID associated with the index;

generate the access ID based on information that identifies the format of the access ID and at least one of the customer type, the customer ID, or the space ID;

store the access ID in one of the one or more spaces of the index,
- the access ID being associated with a base station ID that identifies the base station; and provide the access ID to the user device and provide the access ID to the base station based on the base station ID,
- the access ID permitting the user device to connect to the base station to access a network via the base station.

17. The non-transitory computer-readable medium of claim 16, where the plurality of instructions further cause the one or more processors to:

provision a network device to apply a particular policy to a data flow processed by the base station,
- the particular policy being based on the customer type or the customer ID.

18. The non-transitory computer-readable medium of claim 16, where the instruction to generate the index identifies a quantity of base stations associated with the customer or a quantity of user devices that are to receive access to the base station, the plurality of instructions further cause the one or more processors to:

determine the customer type based on the quantity of base stations or the quantity of user devices, where one or more instructions, of the plurality of instructions, to generate the index or generate the access ID, further cause the one or more processors to generate the index or generate the access ID based on determining the customer type.

19. The non-transitory computer-readable medium of claim 16, where the base station is one of one or more base stations, the plurality of instructions further cause the one or more processors to:

monitor a status of the one or more base stations to identify particular base stations, of the one or more base stations, that are underperforming with respect to a performance parameter; and provide an alert when greater than a threshold quantity or a threshold percentage of the one or more base stations are underperforming,
- the threshold quantity or threshold percentage being based on the customer type or the customer ID.

20. The non-transitory computer-readable medium of claim 16, where the base station is associated with a femto cell, a micro cell, or a macro cell.

* * * * *